United States Patent [19]  [11]  4,272,543
Niedballa et al.  [45]  Jun. 9, 1981

[54] PHARMACOLOGICALLY ACTIVE 4,5-DIARYL-2-SUBSTITUTED-IMIDAZOLES

[75] Inventors: Ulrich Niedballa; Irmgard Bottcher, both of Berlin, Fed. Rep. of Germany

[73] Assignee: Schering, Aktiengesellschaft, Berlin and Bergkamen, Fed. Rep. of Germany

[21] Appl. No.: 107,802

[22] Filed: Dec. 27, 1979

[30] Foreign Application Priority Data

Dec. 28, 1978 [DE] Fed. Rep. of Germany ....... 2856909

[51] Int. Cl.³ .................... A61K 31/415; C07D 233/84
[52] U.S. Cl. ................................ 424/273 R; 548/336; 548/337; 546/256; 424/263
[58] Field of Search ..................... 424/273 R; 548/337

[56] References Cited
U.S. PATENT DOCUMENTS

| 3,488,423 | 1/1970 | Doebel et al. | 548/337 |
| 3,636,003 | 1/1972 | Doebel et al. | 548/337 |
| 3,651,080 | 3/1972 | Doebel et al. | 548/337 |
| 3,842,097 | 10/1974 | Tweit | 548/337 |
| 3,915,980 | 10/1975 | Gebert et al. | 548/337 |
| 4,159,338 | 6/1979 | Cherkofsky et al. | 548/337 |
| 4,182,769 | 1/1980 | Cherkofsky et al. | 548/337 |
| 4,190,666 | 2/1980 | Cherkofsky et al. | 548/337 |

FOREIGN PATENT DOCUMENTS 2635876 3/1977 Fed. Rep. of Germany .

OTHER PUBLICATIONS

Bhatt et al., Current Science, vol. 17, 184–185, 1948.

Primary Examiner—Henry R. Jiles
Assistant Examiner—Jane T. Fan
Attorney, Agent, or Firm—Millen & White

[57] ABSTRACT

Imidazole derivatives of the formula

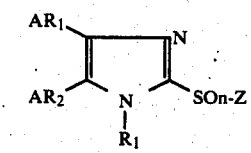

wherein
 AR$_1$ and AR$_2$ are independently each phenyl; phenyl substituted by halogen, C$_{1-4}$ alkyl, C$_{1-4}$ alkoxy or C$_{2-6}$ dialkylamino; pyridyl; furyl; or thienyl; with the proviso that AR$_1$ and AR$_2$ are not both unsubstituted phenyl;
 R$_1$ is hydrogen, alkyl of 1–4 carbon atoms or alkyl of 1–4 carbon atoms substituted by hydroxy, C$_{1-4}$ alkoxy or C$_{1-6}$ alkanoyloxy;
 n is 0, 1 or 2; and
 Z is cyano; alkynyl of 2–6 carbon atoms; cycloalkyl of 3–8 carbon atoms; cycloalkyl of 3–8 carbon atoms substituted by hydroxy, acyloxy, hydroxymethyl or acyloxymethyl, "acyl" in both cases being the acyl group of a hydrocarbon, aliphatic C$_{1-6}$ carboxylic acid or of benzoic acid; or alkyl of 1–4 carbon atoms substituted by cyano, phenyl or cycloalkyl of 3–6 carbon atoms;
or physiologically acceptable salts thereof with an acid, have valuable pharmacological properties.

38 Claims, No Drawings

PHARMACOLOGICALLY ACTIVE 4,5-DIARYL-2-SUBSTITUTED-IMIDAZOLES

The present invention relates to novel imidazole derivatives, a process for their production and pharmaceutical preparations containing these imidazole derivatives as active ingredients.

SUMMARY OF THE INVENTION

It is an object of this invention to provide new imidazole derivatives having valuable pharmacological properties.

Upon further study of the specification and appended claims, further objects and advantages of this invention will become apparent to those skilled in the art.

These objects have been attained by providing imidazole derivatives of formula I

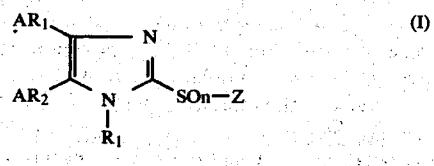

wherein
$AR_1$ and $AR_2$ are independently each phenyl; phenyl substituted by halogen, alkyl, alkoxy or dialkylamino; pyridyl; furyl; or thienyl; with the proviso that $AR_1$ and $AR_2$ are not both unsubstituted phenyl;
$R_1$ is hydrogen, alkyl of 1-4 carbon atoms or alkyl of 1-4 carbon atoms substituted by hydroxy, alkoxy or acyloxy;
n is 0, 1 or 2; and
Z is cyano; alkynyl of 2-6 carbon atoms; cycloalkyl of 3-8 carbon atoms; cycloalkyl of 3-8 carbon atoms substituted by hydroxy, acyloxy, hydroxymethyl, or acyloxymethyl; or alkyl of 1-4 carbon atoms substituted by cyano, phenyl or cycloalkyl of 3-6 carbon atoms; or a physiologically acceptable salt thereof with an acid.

DETAILED DESCRIPTION

The substituents $AR_1$ and $AR_2$ of the imidazole derivatives of this invention can each be phenyl optionally substituted by halogen, alkyl, alkoxy or dialkylamino; pyridyl; furyl; or thienyl. Halogen substituted phenyl residues $AR_1$ and $AR_2$ can contain 1-3 halogen atoms, preferably 1 or 2 halogen atoms, the latter being substituted, preferably in the meta- and para positions. These include, for example, mono- or dichlorophenyl and particularly parafluorophenyl and parachlorophenyl. The alkyl-substituted phenyl groups generally contain 1-2 alkyl groups of preferably 1-4 carbon atoms, for example, methyl, ethyl, propyl or isopropyl. The alkoxy substituted phenyl groups generally contain 1-2 alkoxy groups of preferably 1-4 carbon atoms, e.g., methoxy, ethoxy, propoxy or isopropoxy. Dialkylamino substituted phenyl groups generally contain 1-2 dialkylamino groups, each dialkylamino group preferably having 2-6 total carbon atoms, for example, dimethylamino, methylethylamino or diethylamino.

The pyridyl, furyl or thienyl groups for $AR_1$ or $AR_2$ may be attached via any of their carbon atoms; attachment via the 2-position is preferred in each case.

The substituents $AR_1$ and $AR_2$ can be identical or different with the proviso that only one of these, not both, can be unsubstituted phenyl.

$R_1$ can be hydrogen or alkyl of 1-4 carbon atoms optionally substituted by 1-2 hydroxy, alkoxy or acyloxy groups. Preferably, the substituent $R_1$ is an alkyl group which is unsubstituted or substituted in the 2-position by hydroxy, alkoxy of 1-4 carbon atoms (e.g., methoxy, ethoxy, propoxy or isopropoxy) or acyloxy of 1-6 carbon atoms, e.g., $C_{1-6}$ alkanoyloxy and its equivalents, e.g., formyloxy, acetoxy, propionyloxy or butyryloxy. In particular, $R_1$ is most preferably hydrogen or methyl.

Z can be cyano; alkynyl of 2-6 carbon atoms; cycloalkyl of 3-8 carbon atoms optionally substituted by 1-2 hydroxy, acyloxy, hydroxymethyl or acyloxymethyl groups; or alkyl of 1-4 carbon atoms substituted by 1-2 cyano, phenyl or $C_{3-6}$ cycloalkyl groups.

Examples of suitable alkynyl groups Z include ethynyl 1-propynyl, 2-propynyl, 1-butynyl, 2-butynyl or 3,3-dimethyl-2-butynyl. Examples of suitable cycloalkyl groups Z include cyclopropyl, cyclobutyl, cyclopentyl, cyclohexyl or cycloheptyl. Suitable acyloxy groups for the acyloxy and acyloxymethyl substituents on the cycloalkyl residue Z include, preferably, those groups derived from hydrocarbon aliphatic, preferably saturated, carboxylic acid of 1-6 carbon atoms (e.g., formic acid, acetic acid, propionic acid, butyric acid, isobutyric acid, trimethylacetic acid, valeric acid, etc.) or from benzoic acid and equivalents thereof. The hydroxy, acyloxy, hydroxymethyl or acyloxymethyl groups are preferably in the 2-position of the cycloalkyl residue. Examples of suitable alkyl groups of 1-4 carbon atoms substituted by cyano, cycloalkyl of 3-6 carbon atoms or phenyl include: cyanomethyl, benzyl, cyclopropylmethyl, cyclobutylmethyl, cyclopentylmethyl, cyclohexylmethyl and the like.

The novel imidazole derivatives of Formula I can be prepared according to conventional methods. Suitable processes include those described below which can be conducted under conventional conditions. See, e.g., "Liebigs Annalen" 284: 9 et seq. [1894]; J. Chem. Soc.: 3043 et seq. [1931]; J. Med. Chem. 20: 563 et seq. [1977]; "Liebigs Annalen" 214: 257 et seq. [1882]; J. Chem. Soc.: 232 et seq. [1942]; J. Chem. Soc.: 2195 et seq. [1963]; Houben-Weyl, "Methoden der organischen Chemie" [Methods of Organic Chemistry] IX: 229 et seq.; Bull. Soc. France: 271 et seq. [1977]; DOS [German Unexamined Laid-Open Application] 2,635,876; J. Chem. Soc.: 2185 [1963]; J. Amer. Chem. Soc. 100: 1481 [1978]; and Chem. Ber. [Chemical Reports] 111: 2785 [1978] which disclosures are incorporated by reference herein. These processes include (a) condensing an imidazole derivative of Formula II

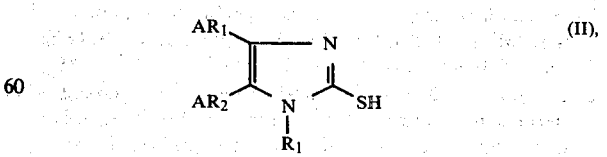

wherein $AR_1$, $AR_2$, and $R_1$ are as defined above, with a compound of Formula III

wherein

Z is as defined above and

W is halogen, alkylsulfonyloxy or arylsulfonyloxy; or (b) for the preparation of imidazole derivatives of Formula I wherein Z is a group of formulae III or IV

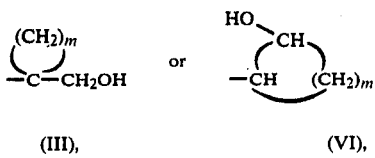

wherein m is 1 to 6, subjecting an epoxide of Formulae V or VI

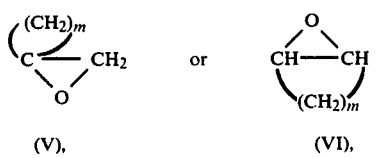

wherein m is defined above, to chemical addition with a mercaptan of Formula II; or (c) for the preparation of imidazole derivatives of Formula I wherein Z is cycloalkyl, reacting a disulfide of Formula VII

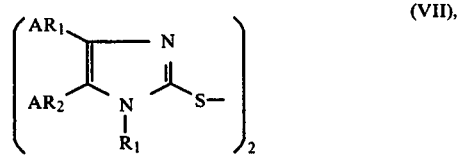

with a cycloalkyllithium compound; and optionally subjecting to alkylation the imidazole derivatives obtained according to process versions (a) through (c) which are unsubstituted in the 1-position; esterifying imidazole derivatives which contain hydroxy groups; oxidizing any present thio groups to sulfynyl groups or sulfonyl groups; and/or converting imidazole derivatives of Formula I with physiologically acceptable acids into the salts thereof.

After synthesis has been effected, racemic imidazole derivatives of Formula I can be split into their optical antipodes by conventional methods, for example, by column chromatography on optically active carriers (e.g., "Sephadex").

The mercapto starting compounds for the processes of this invention are known or can be prepared by conventional methods. (See, e.g., Synthesis: 733 et seq. [1976] and Zhur. Obsch. Khim 31: 1039 et seq. [1961]; Houben-Weyl IX: 59 [1955], which disclosures are incorporated by reference herein.) Typical preparative processes for these starting compounds are described below with reference to several typical compounds.

A solution of 20.43 g of 4-dimethylaminobenzoin in 250 ml of dimethylformamide is combined with 12.18 g of ammonium thiocyanate; and the reaction mixture is heated for 14 hours at 80° C. After cooling, the solution is stirred into ice water, the thus-precipitated crystals are vacuum-filtered and recrystallized from hot ethanol. Yield: 14.62 g of 4-(4-dimethylaminophenyl)-5-phenyl-2-mercaptoimidazole, m.p. 277°–280° C.

A solution of 4.04 g of 2-pyridoin in 50 ml of dimethylformamide is combined with 3.04 g of ammonium thiocyanate, and the solution is heated for 12 hours at 80° C. After cooling, the solution is stirred into ice water, and the thus-precipitated crystals are vacuum-filtered and recrystallized from hot ethanol. Yield: 4.70 g of 4,5-bis(2-pyridyl)-2-mercaptoimidazole, m.p. 285°–287° C.

A solution of 11.2 g of 2-thiophenoin in 150 ml of dimethylformamide is combined with 7.6 g of ammonium thiocyanate; and the solution is heated for 8 hours at 80° C. After cooling, the solution is stirred into ice water, and the thus-precipitated product is vacuum-filtered and recrystallized from hot ethanol. Yield: 7.23 g of 4,5-di(2-thienyl)-2-mercaptoimidazole, m.p. 300°–301° C.

The starting disulfide compounds of Formula VII are new and can prepared according to conventional methods, e.g. by oxidising the corresponding mercapto compound of Formula II with oxidising agents (perhydrol, oxigen, iodine etc.) in an inert solvent (dimethyl formamide, dioxane and/or dichloromethane etc.).

The imidazole derivatives of this invention are distinguished by a pronounced antiinflammatory, antiallergic, and immunostimulating activity.

Moreover, the imidazole derivatives of this invention are advantageously characterized by a very favorable dissociation between desirable pharmacological efficacy and undesirable—especially ulcerogenic—side effects. This dissociation is especially pronounced in those imidazole derivatives of Formula I wherein n is 1 or 2.

Consequently, the novel compounds are suitable, in combination with the vehicles customary in galenic pharmacy, for the treatment of, for example, acute and chronic polyarthritis, neurodermitis, bronchial asthma, hay fever, and other diseases in mammals, including humans.

The drug specialties are prepared in the usual way by converting the active agents together with suitable additives, carrier substances, and flavor-ameliorating agents into the desired forms of application, such as tablets, dragees, capsules, solutions, inhalants, etc.

The pharmacologically active compounds of this invention can be processed in accordance with conventional methods of galenic pharmacy to produce medicinal agents, especially for oral administration to patients, e.g., mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Especially suitable in treating the mentioned indications by oral application are tablets, dragees, and capsules, which contain, for example, 1–250 mg of active ingredient and 50 mg to 2 g of a pharmacologically inert vehicle, such as, for example, lactose, amylose, talc, gelatin, magnesium stearate and similar materials, as well as the usual additives.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A solution of 4.68 g. of 4,5-bis(4-methoxyphenyl)-2-mercaptoimidazole in 120 ml. of dioxane/methanol 1:1 is combined with 2.38 g. of propargyl bromide. The reaction mixture is heated to 60° and then stirred under argon for 2 hours. The mixture is thereafter poured into 400 ml. of dilute sodium bicarbonate solution and extracted with chloroform. The organic solution is dried over sodium sulfate and evaporated to dryness under vacuum. The residue is crystallized from ethyl acetate, thus obtaining 3.63 g. of 4,5-bis(4-methoxyphenyl)-2-(2-propynylthio)imidazole as colorless needles, m.p. 173°–174°.

EXAMPLE 2

A solution of 1.69 g. of 3-chloroperbenzoic acid (80%) in 150 ml. of chloroform is added dropwise to a solution of 2.74 g. of 4,5-bis(4-methoxyphenyl)-2-(2-propynylthio)imidazole in 300 ml. of chloroform. The mixture is stirred overnight at room temperature, then washed with sodium bicarbonate solution; the organic solution is dried over sodium sulfate and concentrated under vacuum. The oily residue is crystallized from ethyl acetate, thus producing 2.08 g. of 4,5-bis(4-methoxyphenyl)-2-(2-propynylsulfynyl)imidazole, m.p. 126°–128°.

EXAMPLE 3

A solution of 4.32 g. of 3-chloroperbenzoic acid (80%) in 200 ml. of chloroform is added dropwise to a solution of 1.75 g. of 4,5-bis(4-methoxyphenyl)-2-(2-propynylthio)imidazole in 250 ml. of chloroform. The mixture is stirred overnight at room temperature, then washed with sodium bicarbonate solution; the organic solution is dried over sodium sulfate and concentrated under vacuum. The residue is crystallized from ethyl acetate, thus obtaining 1.69 g. of 4,5-bis(4-methoxyphenyl)-2-(2-propynylsulfonyl)imidazole, m.p. 151°–153°.

EXAMPLE 4

A mixture of 3.12 g. of 4,5-bis(4-methoxyphenyl)-2-mercaptoimidazole, 1.1 g. of chloromethylcyclopropane, and 100 ml. of ethanol is heated for 4 hours with reflux under argon. After cooling, the reaction mixture is neutralized with 2 N sodium hydroxide solution, poured into 500 ml. of water, and the thus-precipitated solid matter is taken up in methylene chloride. The organic solution is dried over sodium sulfate and concentrated to dryness under vacuum. The residue is crystallized from dibutyl ether, thus producing 2.91 g. of 4,5-bis(4-methoxyphenyl)-2-(cyclopropylmethylthio)imidazole, m.p. 119°.

EXAMPLE 5

1.082 g. of 3-chloroperbenzoic acid (80%) in 100 ml. of methylene chloride is added dropwise to a solution of 1.83 g. of 4,5-bis(4-methoxyphenyl)-2-(cyclopropylmethylthio)-imidazole in 200 ml. of methylene chloride. The reaction mixture is stirred for 2 hours, washed with saturated sodium bicarbonate solution; the organic solution is dried over sodium sulfate and concentrated under vacuum to dryness. The residue is crystallized from dibutyl ether, thus obtaining 1.41 g. of 4,5-bis(4-methoxyphenyl)-2-(cyclopropylmethylsulfynyl)imidazole, m.p. 147°.

EXAMPLE 6

2.164 g. of 3-chloroperbenzoic acid (80%) in 200 ml. of methylene chloride is added dropwise to a solution of 1.83 g. of 4,5-bis(4-methoxyphenyl)-2-(cyclopropylmethylthio)-imidazole in 200 ml. of methylene chloride. The mixture is stirred for 2 hours and washed with saturated sodium bicarbonate solution. The organic solution is dried over sodium sulfate and concentrated to dryness under vacuum. The residue is crystallized from dibutyl ether/ethanol, thus producing 1.43 g. of 4,5-bis(4-methoxyphenyl)-2-(cyclopropylmethylsulfonyl)imidazole, m.p. 149°.

EXAMPLE 7

6.25 g. of 4,5-bis(4-methoxyphenyl)-2-mercaptoimidazole is added to a solution of 1.86 g. of bromomethylcyclopentane in 150 ml. of ethanol. The reaction mixture is heated for 8 hours under argon with reflux. After cooling, the mixture is neutralized with 2 N sodium hydroxide solution, poured into water, and the thus-separated solid matter is taken up in methylene chloride. The organic solution is dried over sodium sulfate and concentrated to dryness under vacuum. The residue is crystallized from methylene chloride/hexane and recrystallized from ethanol. Yield: 6.57 g. of 4,5-bis-(4-methoxyphenyl)-2-(cyclopentylmethylthio)imidazole, m.p. 175°–177°.

EXAMPLE 8

2.164 g. of 2-chloroperbenzoic acid (80%) in 200 ml. of methylene chloride is added dropwise to a solution of 3.94 g. of 4,5-bis(4-methoxyphenyl)-2-(cyclopentylmethylthio)imidazole in 150 ml. of methylene chloride. The mixture is stirred for 2 hours, washed with saturated sodium bicarbonate solution, and the organic solution is dried over sodium sulfate and concentrated to dryness under vacuum. The residue is crystallized from methylene chloride/hexane. Yield: 3.63 g. of 4,5-bis(4-methoxyphenyl)-2-(cyclopentylmethylsulfynyl)imidazole, m.p. 212°–213°.

EXAMPLE 9

4.328 g. of 3-chloroperbenzoic acid (80%) in 400 ml. of methylene chloride is added in incremental portions to a solution of 3.94 g. of 4,5-bis(4-methoxyphenyl)-2-(cyclopentylthio)imidazole in 150 ml. of methylene chloride. The mixture is further stirred for 2 hours, washed with saturated sodium bicarbonate solution, the organic solution is dried over sodium sulfate and concentrated to dryness under vacuum. The residue is crystallized from methylene chloride/hexane, thus obtaining 3.53 g. of 4,5-bis(4-methoxyphenyl)-2-(cyclopentylmethylsulfonyl)imidazole, m.p. 180°–181°.

EXAMPLE 10

A solution of 150 ml. of ethanol and 4.37 g. of bromocyclopentane is combined with 6.25 g. of 4,5-bis(4-methoxyphenyl)-2-mercaptoimidazole and heated under reflux for 12 hours under argon. After cooling, the mixture is neutralized with 2 N sodium hydroxide solution, poured into 700 ml. of water, and the thus-separated solid matter is taken up in methylene chloride. The organic solution is dried over sodium sulfate and concentrated to dryness under vacuum. The amorphous residue is dissolved in ether and made to crystallize after the addition of hexane. After recrystallization from ether/hexane, the yield is 6.08 g. of 4,5-bis-(4-methoxyphenyl)-2-(cyclopentylthio)imidazole, m.p. 169°–170°.

EXAMPLE 11

A solution of 953 mg. of 4,5-bis(4-methoxyphenyl)-2-(cyclopentylthio)imidazole in 150 ml. of methylene chloride is combined with incremental portions of 541 mg. of 3-chloroperbenzoic acid (80%) in 70 ml. of methylene chloride. The mixture is further stirred for 15 minutes, then washed with saturated sodium bicarbonate solution; the organic solution is dried over sodium sulfate and concentrated to dryness under vacuum. The residue is crystallized from methylene chloride/hexane Yield: 920 mg. of 4,5-bis(4-methoxyphenyl)-2-(cyclopentylsulfynyl)imidazole as colorless needles, m.p. 159°–160°.

EXAMPLE 12

A solution of 953 mg. of 4,5-bis(4-methoxyphenyl)-2-(cyclopentylthio)imidazole in 150 ml. of methylene chloride is combined with incremental portions of 1082 mg. of 3-chloroperbenzoic acid (80%) in 100 ml. of methylene chloride. The mixture is stirred for 15 minutes and washed with saturated sodium bicarbonate solution. The organic solution is dried over sodium sulfate and concentrated to dryness under vacuum. The residue is crystallized from methylene chloride/hexane, thus obtaining 800 mg. of 4,5-bis(4-methoxyphenyl)-2-(cyclopentylsulfonyl)imidazole as pink needles, m.p. 152°–153°.

EXAMPLE 13

3.12 g. of 4,5-bis(4-methoxyphenyl)-2-mercaptoimidazole is dissolved in 100 ml. of a 0.1 N sodium ethylate solution, combined with 1.1 g. of cyclopentene oxide and heated with reflux under argon for 12 hours. After cooling, the mixture is poured into 500 ml. of water. The thus-precipitated solid matter is taken up in methylene chloride, and the organic solution is dried over sodium sulfate and concentrated to dryness under vacuum. The residue is crystallized from cyclohexane/ethanol, thus producing 3.19 g. of 4,5-bis(4-methoxyphenyl)-2-(2-hydroxycyclopentylthio)imidazole, m.p. 103°–105°.

EXAMPLE 14

1.082 g. of 3-chloroperbenzoic acid (80%) in 100 ml. of methylene chloride is added dropwise to a solution of 1.98 g. of 4,5-bis(4-methoxyphenyl)-2-(2-hydroxycyclopentylthio)imidazole in 200 ml. of methylene chloride. The mixture is stirred for 2 hours and washed with saturated sodium bicarbonate solution. The organic solution is dried over sodium sulfate and concentrated to dryness under vacuum. The residue is crystallized from methylene chloride/hexane, thus obtaining 1.66 g. of 4,5-bis(4-methoxyphenyl)-2-(2-hydroxycyclopentylsulfynyl)imidazole, m.p. 194°–196°.

EXAMPLE 15

2.164 g. of 3-chloroperbenzoic acid (80%) in 200 ml. of methylene chloride is added dropwise to a solution of 1.98 g. of 4,5-bis(4-methoxyphenyl)-2-(2-hydroxycyclopentylthio)imidazole in 200 ml. of methylene chloride. The mixture is stirred for 2 hours, washed with saturated sodium bicarbonate solution; the organic solution is dried over sodium sulfate and concentrated to dryness under vacuum. The residue is crystallized from methylene chloride/hexane, thus producing 1.73 g. of 4,5-bis(4-methoxyphenyl)-2-(2-hydroxycyclopentylsulfonyl)imidazole, m.p. 176°–177°.

EXAMPLE 16

400 mg. of acetyl chloride in 10 ml. of absolute tetrahydrofuran is added dropwise to a solution of 1.98 g. of 4,5-bis(4-methoxyphenyl)-2-(2-hydroxycyclopentylthio)imidazole and 560 mg. of triethylamine in 60 ml. of absolute tetrahydrofuran. The mixture is stirred overnight at room temperature. The solution is concentrated under vacuum to about 20 ml. and distributed between 2 N hydrochloric acid and methylene chloride. The methylene chloride solution is washed with sodium bicarbonate, dried over magnesium sulfate, and concentrated to dryness under vacuum. The residue is crystallized from methylene chloride/hexane, thus obtaining 1.79 g. of 4,5-bis(4-methoxyphenyl)-2-(2-acetoxycyclopentylthio)-imidazole in the form of an amorphous foam.

$C_{24}H_{26}N_2O_4S$ (438.550): Calculated: 65.73% C, 5.98% H, 6.39% N, 7.31% S: Found: 65.51, 6.09, 6.33, 7.26.

EXAMPLE 17

1.66 g. of chloroacetonitrile in 20 ml. of ethanol is added to a warm solution of 6.25 g. of 4,5-bis(4-methoxyphenyl)-2-mercaptoimidazole in 100 ml. of ethanol, and the mixture is heated for 24 hours with reflux under argon. The solvent is then removed under vacuum, and the residue is distributed between chloroform and sodium bicarbonate solution. The organic solution is dried over sodium sulfate, concentrated to dryness under vacuum, and the residue is crystallized from ethyl acetate/hexane, thus obtaining 4.16 g. of [4,5-bis(4-methoxyphenyl)-2-imidazolythio]acetonitrile, m.p. 144°.

EXAMPLE 18

A solution of 12.5 g. of 4,5-bis(4-methoxyphenyl)-2-mercaptoimidazole in 800 ml. of dioxane/methylene chloride 3:1 is combined with 4.50 ml. of perhydrol. The mixture is stirred for 4 hours at room temperature, and then the solution is concentrated under vaccum to 100 ml. The thus-formed product is allowed to crystallize from the solution, thus obtaining 9.66 g. of bis[4,5-bis(4-methoxyphenyl)-2-imidazolyl]disulfide, m.p. 249°.

EXAMPLE 19

A solution of 9.33 g. of bis[4,5-bis(4-methoxyphenyl)-2-imidazolyl]disulfide in 100 ml. of absolute hexamethylphosphoric triamide is combined with 1.584 g. of sodium hydride (50%, in white oil). The mixture is stirred for 30 minutes at room temperature, then combined with 3.42 g. of trimethylchlorosilane, and stirred for another 3 hours at room temperature. The mixture is blanketed with argon, and 30 ml. of an approximately 0.9 N cyclopropyllithium solution in ether is added dropwise under agitation. After this step, the mixture is stirred for another 4 hours at 60°. The thus-obtained solution is poured into 600 ml. of ice water and extracted with ether. The organic solution is washed with water, dried over sodium sulfate, and concentrated to dryness under vacuum. The residue is purified by column chromatography on 300 g. of silica gel with cyclohexane/ethyl acetate 1:1, thus obtaining 1.93 g. of 4,5-bis(4-methoxyphenyl)-2-(cyclopropylthio)imidazole, produced as an amorphous foam when the solvent is evaporated.

$C_{20}H_{20}N_2O_2S$ (352.458): Calculated: 68.16% C, 5.27% H, 7.95% N, 9.10% S: Found: 68.04, 5.82, 7.91, 9.01.

From ether/hexane, crystals are produced which melt at 135°.

EXAMPLE 20

Under the conditions of Example 5, 1.76 g. of 4,5-bis(4-methoxyphenyl)-2-(cyclopropylthio)imidazole is oxidized. Crystallization from ether yields 1.53 g. of 4,5-bis(4-methoxyphenyl)-2-(cyclopropylsulfynyl)imidazole, m.p. 180°.

EXAMPLE 21

Under the conditions of Example 6, 1.76 g. of 4,5-bis(4-methoxyphenyl)-2-(cyclopropylthio)imidazole is oxidized. Crystallization from dibutyl ether yields 1.52 g. of 4,5-bis-(4-methoxyphenyl)-2-(cyclopropylsulfonyl)imidazole, m.p. 176°.

EXAMPLE 22

A mixture of 2.88 g. of 4,5-bis(4-fluorophenyl)-2-mercaptoimidazole and 1.1 g. of chloromethylcyclopropane in 100 ml. of absolute ethanol is heated with reflux under argon for 4 hours. The cooled solution is neutralized with 2 N sodium hydroxide solution, poured into 500 ml. of water, and the thus-precipitated product is vacuum-filtered, washed with water, and dried under vacuum at 60°, thus producing 2.67 g. of 4,5-bis(4-fluorophenyl)-2-(cyclopropylmethylthio)imidazole, m.p. 210°–211°.

EXAMPLE 23

Under the conditions of Example 5, 1.71 g. of 4,5-bis(4-fluorophenyl)-2-(cyclopropylmethylthio)imidazole is oxidized, thus obtaining after evaporating the solvent 1.34 g. of 4,5-bis(4-fluorophenyl)-2-(cyclopropylmethylsulfynyl)-imidazole, m.p. 181°–183° (methylene chloride/hexane).

EXAMPLE 24

Under the conditions of Example 6, 1.71 g. of 4,5-bis(4-fluorophenyl)-2-(cyclopropylmethylthio)imidazole is oxidized. After withdrawing the solvent, 1.47 g. of 4,5-bis-(4-fluorophenyl)-2-(cyclopropylmethylsulfonyl)imidazole is obtained, m.p. 251° (methylene chloride/hexane).

EXAMPLE 25

A mixture of 2.64 g. of 4,5-di(2-thienyl)-2-mercaptoimidazole, 1.1 g. of chloromethylcyclopropane, and 60 ml. of absolute ethanol is heated under reflux for 8 hours under argon. After cooling, the mixture is neutralized with 2 N sodium hydroxide solution, poured into 300 ml. of water, and the thus-precipitated product is taken up in methylene chloride, dried over sodium sulfate, and the solution is concentrated to dryness under vaccum. The residue is crystallized from methylene chloride/hexane, thus producing 2.36 g. of 4,5-di(2-thienyl)-2-(cyclopropylmethylthio)imidazole, m.p. 185°–187°.

EXAMPLE 26

Under the conditions of Example 5, 1.59 g. of 4,5-bis(2-thienyl)-2-(cyclopropylmethylthio)imidazole is oxidized, yielding after withdrawal of the solvent 1.24 g. of 4,5-bis-(2-thienyl)-2-(cyclopropylmethylsulfynyl)imidazole, m.p. 156°–157° (methylene chloride/hexane).

EXAMPLE 27

Under the conditions of Example 6, 1.59 g. of 4,5-bis(2-thienyl)-2-(cyclopropylmethylthio)imidazole is oxidized. After moving the solvent by evaporation, 1.56 g. of 4,5-bis-(2-thienyl)-2-(cyclopropylmethylsulfonyl)imidazole is obtained as an amorphous foam.

$C_{15}H_{14}N_2O_2S_3$ (350.480): Calculated: 51.41% C, 4.03% H, 7.99% N, 27.44% S: Found: 51.27, 4.10, 7.85, 27.36.

EXAMPLE 28

2.54 g of 4,5-bis(2-pyridyl)-2-mercaptoimidazole is dissolved in 100 ml. of a 0.1 N sodium ethylate solution and combined with 1.1 g. of chloromethylcyclopropane. The mixture is heated for 8 hours with reflux under argon, allowed to cool, and the solution poured into 800 ml. of water. The mixture is saturated with sodium chloride and the product extracted with ethyl acetate. The organic solution is dried over sodium sulfate and concentrated to dryness under vacuum, thus obtaining 2.38 g. of 4,5-bis(2-pyridyl)-2-(cyclopropylmethylthio)imidazole as an amorphous foam.

$C_{17}H_{16}N_4S$ (308.409): Calculated: 66.21% C, 5.23% H, 18.18% N, 10.40% S: Found: 65.94, 5.31, 18.11, 10.35.

The compound is dissolved in absolute ethanol and combined with ethereal HCl. The yellow product, 4,5-bis-(2-pyridyl)-2-(cyclopropylmethylthio)imidazole hydrochloride, is crystallized, melting at 200°–202°.

EXAMPLE 29

Under the conditions of Example 5, 1.54 g. of 4,5-bis(2-pyridyl)-2-(cyclopropylmethylthio)imidazole is oxidized, thus obtaining 1.17 g. of 4,5-bis(2-pyridyl)-2-(cyclopropylmethylsulfynyl)imidazole, m.p. 166°–168° (methylene chloride/hexane).

EXAMPLE 30

Under the conditions of Example 6, 1.54 g. of 4,5-bis(2-pyridyl)-2-(cyclopropylmethylthio)imidazole is oxidized. After evaporation of the solvent, 1.12 g. of 4,5-bis(2-pyridyl)-2-(cyclopropylmethylsulfonyl)imidazole is obtained, m.p. 210°-212° (methylene chloride/ethanol).

EXAMPLE 31

Under agitation and blanketing with argon, 3.81 g. of 4,5-bis(4-methoxyphenyl)-2-(cyclopentylthio)imidazole is dissolved in a solution of 300 mg. of sodium in 150 ml. of absolute ethanol. Then, 1.85 g. of methyl iodide is added thereto, and the mixture is heated overnight under reflux. After cooling, the mixture is poured into 600 ml. of water; the thus-precipitated product is taken up in methylene chloride. The organic solution is dried over sodium sulfate and concentrated under vacuum to dryness. The residue is crystallized from methanol, thus obtaining 2.49 g. of 4,5-bis(4-methoxyphenyl)-1-methyl-2-(cyclopentylthio)imidazole, m.p. 122°-124°.

EXAMPLE 32

Analogous to Example 13, using the corresponding appropriate reactants, 4,5-bis(4-methoxyphenyl)-2-(2-hydroxymethylcyclopropylthio)imidazole, is prepared.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. An imidazole derivative of the formula

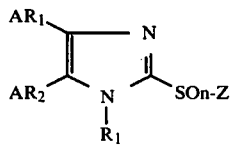

$AR_1$ and $AR_2$ are independently each phenyl; or phenyl substituted by halogen, $C_{1-4}$ alkyl, $C_{1-4}$ alkoxy or $C_{2-6}$ dialkylamino; with the proviso that $AR_1$ and $AR_2$ are not both unsubstituted phenyl;

$R_1$ is hydrogen, alkyl of 1-4 carbon atoms or alkyl of 1-4 carbon atoms substituted by hydroxy, $C_{1-4}$ alkoxy or $C_{1-6}$ alkanoyloxy;

n is 0, 1 or 2; and

Z is cyano; alkynyl of 2-6 carbon atoms; cycloalkyl of 3-8 carbon atoms; cycloalkyl of 3-8 carbon atoms substituted by hydroxy, acyloxy, hydroxymethyl or acyloxymethyl, "acyl" in both cases being the acyl group of a hydrocarbon, aliphatic $C_{1-6}$ carboxylic acid or of benzoic acid; or alkyl of 1-4 carbon atoms substituted by cyano or cycloalkyl of 3-6 carbon atoms;

or a physiologically acceptable salt thereof with an acid.

2. An imidazole derivative of claim 1, wherein $AR_1$ and $AR_2$ are each phenyl; or phenyl substituted in the paraposition by fluorine, chlorine, alkyl of 1-4 carbon atoms, alkoxy of 1-4 carbon atoms or dialkylamino of 2-6 carbon atoms.

3. An imidazole derivative of claim 1, wherein $AR_1$ and $AR_2$ are independently each phenyl, 4-fluorophenyl, 4-chlorophenyl, 4-methylphenyl, 4-methoxyphenyl or 4-dimethylaminophenyl.

4. An imidazole derivative of claim 1, wherein $R_1$ is hydrogen, alkyl of 1-4 carbon atoms, 2-hydroxyethyl or $C_{1-6}$ alkanoyloxyethyl.

5. An imidazole derivative of claim 1, wherein n is 1 or 2.

6. An imidazole derivative of claim 1, wherein Z is cyano.

7. An imidazole derivative of claim 1, wherein Z is alkynyl of 3-6 carbon atoms.

8. An imidazole derivative of claim 1, wherein Z is cycloalkyl of 3-7 carbon atoms.

9. An imidazole derivative of claim 1, wherein Z is methyl substituted by cycloalkyl of 3-6 carbon atoms.

10. 4,5-Bis(4-methoxyphenyl)-2-(2-propynylthio)imidazole, a compound of claim 1.

11. 4,5-Bis(4-methoxyphenyl)-2-(2-propynylsulfynyl)-imidazole, a compound of claim 1.

12. 4,5-Bis(4-methoxyphenyl)-2-(propynylsulfonyl)imidazole, a compound of claim 1.

13. 4,5-Bis(4-methoxyphenyl)-2-(cyclopropylmethylthio)imidazole, a compound of claim 1.

14. 4,5-Bis(4-methoxyphenyl)-2-(cyclopropylmethylsulfynyl)imidazole, a compound of claim 1.

15. 4,5-Bis(4-methoxyphenyl)-2-(cyclopropylmethylsulfonyl)imidazole, a compound of claim 1.

16. 4,5-Bis(4-methoxyphenyl)-2-(cyclopentylmethylthio)imidazole, a compound of claim 1.

17. 4,5-Bis(4-methoxyphenyl)-2-(cyclopentylmethylsulfynyl)imidazole, a compound of claim 1.

18. 4,5-Bis(4-methoxyphenyl)-2-(cyclopentylmethylsulfonyl)imidazole, a compound of claim 1.

19. 4,5-Bis(4-methoxyphenyl)-2-(cyclopentylthio)imidazole, a compound of claim 1.

20. 4,5-Bis(4-methoxyphenyl)-2-(cyclopentylsulfynyl)-imidazole, a compound of claim 1.

21. 4,5-Bis(4-methoxyphenyl)-2-(cyclopentylsulfonyl)imidazole, a compound of claim 1.

22. 4,5-Bis(4-methoxyphenyl)-2-(2-hydroxycyclopentylthio)imidazole, a compound of claim 1.

23. 4,5-Bis(4-methoxyphenyl)-2-(2-hydroxycyclopentylsulfynyl)imidazole, a compound of claim 1.

24. 4,5-Bis(4-methoxyphenyl)-2-(2-hydroxycyclopentylsulfonyl)imidazole, a compound of claim 1.

25. 4,5-Bis(4-methoxyphenyl)-2-(2-acetoxycyclopentylthio)imidazole, a compound of claim 1.

26. {4,5-Bis(4-methoxyphenyl)-2-imidazolylthio}-acetonitrile, a compound of claim 1.

27. 4,5-Bis(4-methoxyphenyl)-2-(cyclopropylthio)-imidazole, a compound of claim 1.

28. 4,5-Bis(4-methoxyphenyl)-2-(cyclopropylsulfynyl)imidazole, a compound of claim 1.

29. 4,5-Bis(4-methoxyphenyl)-2-(cyclopropylsulfonyl)imidazole, a compound of claim 1.

30. 4,5-Bis(4-fluorophenyl)-2-(cyclopropylmethylthio)imidazole, a compound of claim 1.

31. 4,5-Bis(4-fluorophenyl)-2-(cyclopropylmethylsulfynyl)imidazole, a compound of claim 1.

32. 4,5-Bis(4-fluorophenyl)-2(cyclopropylmethylsulfonyl)imidazole, a compound of claim 1.

33. 4,5-Bis(4-methoxyphenyl)-1-methyl-2-(cyclopentylthio)imidazole, a compound of claim 1.

34. 4,5-Bis(4-methoxyphenyl)-2-(2-hydroxymethylcyclopropylthio)imidazole, a compound of claim 1.

35. A pharmaceutical composition comprising an antiinflammatorily effective amount of a compound of claim 1 and a pharmaceutically acceptable carrier.

36. An antiinflammatory composition comprising 1–250 mg of a compound of claim 1 and 50 mg–2 g of a pharmaceutically acceptable carrier.

37. A method of treating inflammations in a mammal which comprises administering an antiinflammatorily effective amount of a compound of claim 1 to the mammal.

38. A method of treating an allergic disease in a mammal which comprises administering to the mammal an amount of a compound of claim 1 effective to treat the allergic disease.

* * * * *